United States Patent [19]

Gramlich et al.

[11] Patent Number: 4,837,201
[45] Date of Patent: Jun. 6, 1989

[54] 4-METHYL-4-PHENYL-1-PENTANALS, THEIR PREPARATION AND THEIR USE AS SCENTS

[75] Inventors: Walter Gramlich, Edingen-Neckarhausen; Norbert Goetz, Worms; Hardo Siegel, Speyer; Gerhard Schindler, Mannheim, all of Fed. Rep. of Germany

[73] Assignee: BASF Aktiengesellschaft, Ludwigshafen, Fed. Rep. of Germany

[21] Appl. No.: 194,892

[22] Filed: May 17, 1988

[30] Foreign Application Priority Data

May 19, 1987 [DE] Fed. Rep. of Germany ..... 3716730

[51] Int. Cl.4 .......................... A61K 7/46; C07C 47/52
[52] U.S. Cl. ...................... 512/26; 568/425; 568/426
[58] Field of Search .............. 512/26, 27; 568/425, 568/426

[56] References Cited

U.S. PATENT DOCUMENTS

| | | | |
|---|---|---|---|
| 4,008,276 | 2/1977 | Zenitz | 568/425 |
| 4,486,607 | 12/1984 | Webb | 568/425 |
| 4,709,109 | 11/1987 | Sperling et al. | 585/438 |

FOREIGN PATENT DOCUMENTS

| | | | |
|---|---|---|---|
| 3141301 | 4/1983 | Fed. Rep. of Germany | 585/425 |
| 3536929 | 4/1987 | Fed. Rep. of Germany | 585/438 |

OTHER PUBLICATIONS

Journal of Organic Chemistry, vol. 29, No. 7, pp. 1663–1669, Free-Radical Rearrangements, Jul. 13, 1964.

Arctander, Parfume and Flavor Chemicals, Montclair 1969, 2172 and 2204.

J. Am. Chem. Soc., vol. 65, pp. 1469–1471, Aug. 1943, Formation of Cyclopropanes from Monohalides. Whitmore et al.

*Primary Examiner*—Werren B. Lone
*Attorney, Agent, or Firm*—Oblon, Spivak, McClelland, Maier & Neustadt

[57] ABSTRACT

4-methyl-4-phenyl-1-pentanals of the general formula I

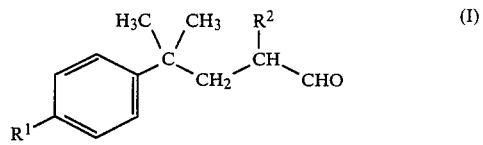

where $R^1$ is hydrogen or $C_1$-$C_4$-alkyl and $R^2$ is hydrogen or methyl, with the exception of 4-methyl-4-phenyl-1-pentanal, and the use of the methylphenylpentanals of the formula I for imparting fragrance properties to, or improving or modifying the fragrance properties of, perfumes and perfumed products, and the preparation of these compounds by hydroformylation of the corresponding 3-methyl-3-phenyl-1-butenes of the general formula II

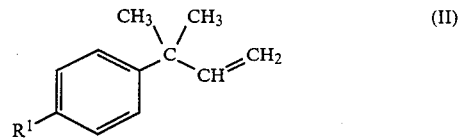

and, if required, subsequent reaction with formaldehyde and partial hydrogenation.

9 Claims, No Drawings

4-METHYL-4-PHENYL-1-PENTANALS, THEIR PREPARATION AND THEIR USE AS SCENTS

The present invention relates to 4-methyl-4-phenyl-1-pentanals of the general formula I

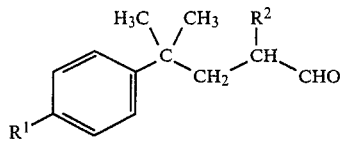

where $R^1$ is hydrogen or $C_1-C_4$-alkyl and $R^2$ is hydrogen or methyl, with the exception of 4-methyl-4-phenyl-1-pentanal, and the preparation and use of 4-methyl-4-phenyl-1-pentanals of the general formula I for imparting a fragrance to, or improving or modifying, perfumes and perfumed products, and perfume compositions.

The 4-methyl-4-phenyl-1-pentanals of the general formula I are novel compounds which have particularly useful fragrance properties. Only 4-methyl-4-phenyl-1-pentanal is not novel.

The compound has already been described by W. H. Urry et al. in J. Org. Chem. 29 (1964), 1663–1669, in an article entitled Free-Radical Rearrangements, II, Ketones and Esters from the Reactions of Aldehydes with Peroxides; however, the article gives no indication of the interesting olfactory properties of this compound.

We have found, surprisingly, that 4-methyl-4-phenyl-1-pentanal is a scent which possesses a very interesting fresh herbaceous fragrance with a woody note and has interesting effects in compositions.

The novel 4-methyl-4-phenyl-1-pentanals are also colorless liquids which have very interesting notes.

A number of compounds having a certain structural relationship with the novel compounds are already known. Examples are:

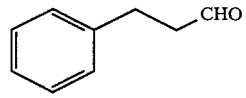

A.

3-phenylpropanal (dihydrocinnamaldehyde)

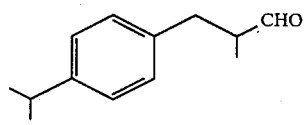

B.

2-methyl-3-(4-isopropylphenyl)-propanal (cyclamenaldehyde)

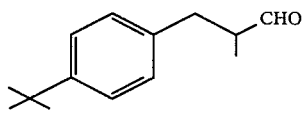

C.

2-methyl-3-(4-tert-butylphenyl)-propanal (Lilial ®/Givaudan)

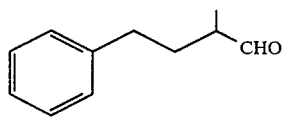

D.

2-methyl-4-phenylbutanal

-continued and

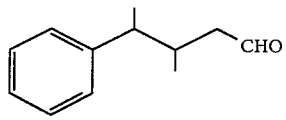

E.

3-methyl-4-phenylvaleraldehyde

The compound stated under A has a strongly floral fragrance with a weakly balsamic note and a strong hyacinth note.

The compounds stated under B and C both have an intense lily-of-the-valley fragrance.

According to Arctander (Perfume and Flavor Chemicals, Montclair 1969, Monograph, pages 2172 and 2204), the compounds stated under D and E have a floral, green fruity fragrance.

The compounds of the general formula I also have very useful fragrance properties which however differ very substantially from the notes of the known, structurally related compounds.

According to J. Org. Chem. 29, 1663–1669, 4-methyl-4-phenyl-1-pentanal (Ia) is prepared in the following manner:

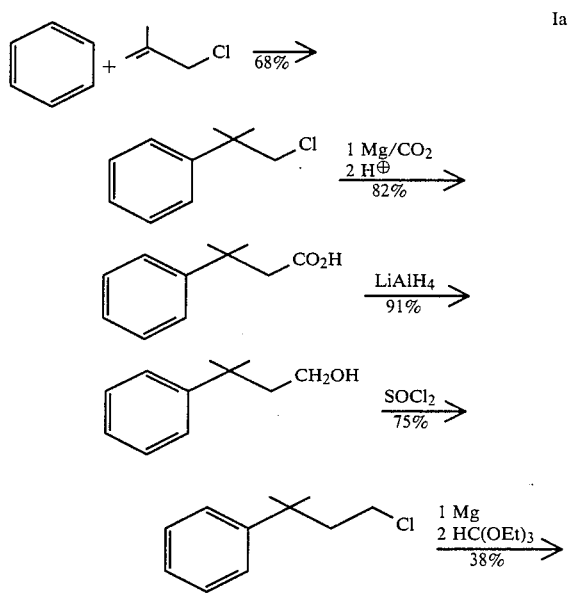

The 1-chloro-2-methyl-2-phenylpropane which can be prepared according to F. C. Withmore et al., J. Am. Chem. Soc. 65 (1943), 1469 by reacting benzene with methallyl chloride is converted in a yield of 82% by a Grignard reaction and subsequent working up with dry ice and hydrolysis into 3-methyl-3-phenylbutyric acid, the latter is reduced (91% yield) with lithium alanate to the alcohol, this is chlorinated in a further step with thionyl chloride in a yield of 75%, and the resulting 1-chloro-3-methyl-3-phenylpropane is reacted with magnesium and then with ethyl orthoformate to give 4-methyl-4-phenyl-1-pentanal in a yield of only 38%. The total yields obtained in this process are only about 21%. Another disadvantage is the fact that some of the reaction steps used are very expensive. In contrast, Ia as well as other, novel 4-methyl-4-phenyl-1-pentanals of the general formula I can be prepared with surprisingly good olfactory properties, in a simple manner and in good yields from 3-methyl-3-phenyl-1-butenes of the general formula II (cf. the previously unpublished patent application No. P 35 36 929.9), which has recently become very readily available.

The present invention therefore also relates to a process for the preparation of 4-methyl-4-phenyl-1-pentanals of the general formula I, wherein A. the corresponding 3-methyl-3-phenyl-1-butene of the general formula II

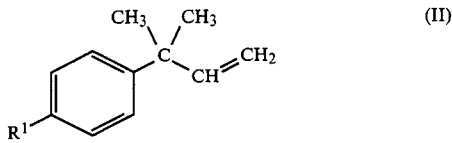

where $R^1$ has the meanings stated in claim 1, is hydroformylated in a conventional manner, B. the resulting methylphenylpentanal of the general formula I, where $R^2$ is hydrogen, is, if required, reacted with formaldehyde to give an unsaturated compound of the general formula III

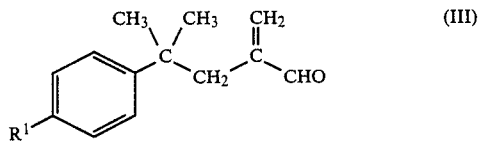

and

C. this is then selectively hydrogenated to give the corresponding α-methylphenylpentanal of the general formula I, where $R^2$ is methyl.

The reaction conditions of the hydroformylation step can be varied within wide limits.

The reaction temperature is in general from 60° to 180° C., preferably from 80° to 110° C.

The hydrogen/carbon monoxide pressure is generally from 20 to 650 bar.

The hydroformylation catalysts generally used are rhodium compounds. They are generally used in amounts corresponding to 0.1–0.5% by weight, based on the butenes of the formula II, of rhodium. Amounts of from 5 to 200 ppm have proven particularly useful. The reaction can be carried out using rhodium carbonyl complexes or other rhodium compounds which form rhodium carbonyl compounds under the reaction conditions, for example the halides, oxides, chelates or fatty acid salts of rhodium.

Rhodium complexes or salts which dissolve in the reaction mixture to give a homogeneous solution, such as dimeric rhodium carbonyl chloride, dimeric cycloocta-1,5-dien-1-yl-rhodium chloride, rhodium carbonyl acetylacetonate or rhodium 2-ethylhexanoate, are particularly advantageous.

The reaction takes place in a particularly advantageous manner if it is additionally carried out in the presence of a triarylphosphine or a phosphite, such as triphenylphosphine or triphenyl phosphite.

The triarylphosphines or the phosphites are used in up to a 100-fold molar excess, based on rhodium.

After removal of the catalyst, the hydroformylation products are isolated from the reaction mixture in a conventional manner, for example by distillation.

In this hydroformylation step, 4-methyl-4-phenyl-1-pentanals of the general formula I, where $R^2$ is hydrogen, are obtained.

These compounds can, if desired, then be reacted with formaldehyde in the form of its aqueous solution or in the form of paraformaldehyde, in the presence of a catalyst, to give an unsaturated compound of the formula III.

Suitable catalysts for this purpose are the amines or enamines described in the literature and obtained from the aldehyde to be reacted and, for example, piperidine, pyrrolidone or morpholine, or mixtures of amines with weak acids, such as oxalic acid. This reaction is preferably carried out under atmospheric pressure at from 90° to 110° C.

For the subsequent selective hydrogenation to give the saturated aldehyde of the general formula I, where $R^2$ is methyl, noble metal catalysts, such as palladium, are preferably used. These are generally used on carriers, such as alumina, titanium dioxide or active carbon. The catalysts contain in general about 0.1–5, preferably 0.5–1, % by weight, based on the carrier, of noble metal.

The hydrogenation conditions essentially depend on the amount and content of the catalyst used.

If a hydrogenation catalyst containing 0.5% by weight of palladium is used in an amount of 10% by weight, based on the unsaturated aldehyde, the reaction generally takes place at from 80° to 140° C. and under a hydrogen pressure of 5 to 50 bar.

The hydrogenation can be carried out with or without a solvent. Solvents which may be used are hydrocarbons, such as cyclohexane, alcohols, such as methanol, or esters, such as ethyl acetate.

The crude products obtained after removal of the catalyst are advantageously purified by fractional distillation.

The 4-methyl-4-phenyl-1-pentanals of the general formula I are colorless liquids which have very interesting fragrance notes.

Because of its interesting fragrance, 4-methyl-4-phenyl-1-pentanal, even in small doses, imparts expression and radiance to compositions of the Fougère and Chypre type.

It has good adhesion and can be readily combined with conventional perfume ingredients and other scents, to give novel compositions.

The most important of the novel compounds of the formula I is 2,4-dimethyl-4-phenylpentanal. It has an interesting green fragrance of fresh leaves with an additional woody note.

The novel compounds of the formula I can be very readily combined with the conventional perfume ingredients and other scents to give novel compositions, to which they impart a particular freshness.

The amount of 4-methyl-4-phenyl-1-pentanals in the scent compositions is in general from 1 to 50% by weight.

The compositions prepared in this manner can be used either directly in fine perfumery or for perfuming cosmetic preparations, such as creams, lotions, toilet waters, soaps, oral hygiene agents and aerosols, or in extract perfumery. They can also be used for improving the odor of industrial products, such as cleaners and detergents, disinfectants and fabric softeners. From 0.05 to 2% by weight, based on the total product, of such a composition are usually used.

The novel scents can be used individually or, in particular, as a mixture with other scents. The Examples which follow illustrate the invention.

EXAMPLE 1

A. Preparation of 4-methyl-4-phenyl-1-pentanal (Ia)

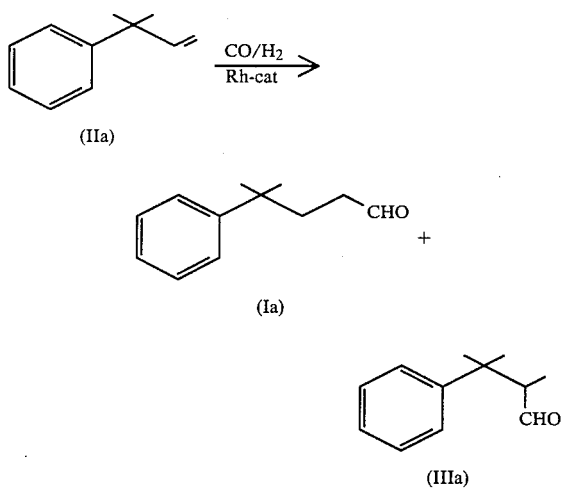

710 g of 3-methyl-3-phenyl-1-butene, 42.7 mg of [Rh-cycloocta-1,5-dienyl Cl]$_2$ (100 ppm) and 1.42 g of triphenylphosphine (1,000 ppm) were initially taken in a 1 l high-pressure autoclave with a magnetic stirrer. 1:1 CO/H$_2$ was forced in at room temperature to a pressure of 100 bar, after which the mixture was heated to 100° C. The CO/H$_2$ (1:1) pressure was then increased to 300 bar. The pressure and temperature were kept constant for 12 hours, after which the mixture was cooled and the pressure let down.

Analysis by gas chromatography (GC) gave a conversion of 94%. The ratio of 4-methyl-4-phenyl-1-pentanal (Ia) to 2,3-dimethyl-3-phenyl-1-butanal (IIIa) was 93:7. Ia could readily be separated from IIIa by distillation.

Pure 4-methyl-4-phenylpentanal was obtained in a yield of 82%, based on IIa. Bp.=70° C./0.01 mbar, $n_D^{25}$=1.5131 Fragrance: fresh herbaceous with a woody note. B. Use of Ia for modifying a perfume composition of the Fougère type (A)

|  | A | B |
|---|---|---|
| Anisaldehyde (BASF) | 30 | 30 |
| Linalool (BASF) | 150 | 150 |
| Lavandin oil abrialis | 50 | 50 |
| Lavender oil Mont Blanc | 70 | 70 |
| α-Hexylcinnamaldehyde | 50 | 50 |
| Lilial* (Givaudan) | 50 | 50 |
| Phenylethanol st. (BASF) | 50 | 50 |
| Amyl salicylate | 20 | 20 |
| Cyclohexylethyl acetate (BASF) | 30 | 30 |
| Tunisian rosemary oil | 30 | 30 |
| Sandelether* (BASF) | 40 | 40 |
| Musk Ether* (FDO) | 40 | 40 |
| Geraniol | 30 | 30 |
| Citronellol (BASF) | 30 | 30 |
| Coumarin | 20 | 20 |
| Vetiver oil Haiti | 20 | 20 |
| Patchouli oil Singapore | 20 | 20 |
| Labdanum extract | 20 | 20 |
| Sytrene acetate | 20 | 20 |
| Geranium oil Bourbon | 20 | 20 |
| Eucalyptus oil glob. | 10 | 10 |
| Oak moss extract | 10 | 10 |
| Lavandin* absolute | 10 | 10 |
| Opopanax extract | 20 | 20 |
| Eugenol | 10 | 10 |
| Hedione* | 10 | 10 |
| Hydroxycitronellal (BASF) | 50 | 50 |
| Dipropylene glycol | 90 | 0 |
| 4-methyl-4-phenyl-1-pentanal | 0 | 90 |
|  | 1000 | 1000 |

*Registered trade mark

The known perfume composition A whose composition is described above has a fresh herbaceous character. If 90 parts of dipropylene glycol are replaced by the novel 4-methyl-4-phenyl-1-pentanal (composition B), the result is to round off lightly and modify the green basic note of the composition. The composition containing Ia moreover has better propagation and an increasing body.

The composition is particularly suitable for bath preparations.

EXAMPLE 2

4-methyl-4-(p-methylphenyl)-1-pentanal (Ib)

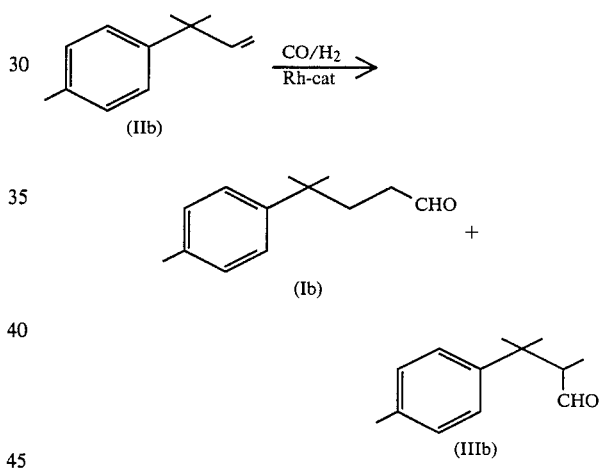

710 g (4.4 moles) of 3-methyl-3-(p-methylphenyl)-1-butene, 42.7 mg of [Rh-cycloocta-1,5-dienyl Cl]$_2$ (100 ppm) and 1.42 g of triphenylphosphine (1,000 ppm) were initially taken in a 1 l high-pressure autoclave equipped with a magnetic stirrer. 1:1 CO/H$_2$ was forced in at room temperature to a pressure of 100 bar, after which the mixture was heated to 100° C. The CO/H$_2$ (1:1) pressure was then increased to 300 bar. The pressure and temperature were kept constant for 12 hours, after which the mixture was cooled and the pressure let down.

GC analysis gave a conversion of 94%. The ratio of 4-methyl-4-(p-methylphenyl)-1-pentanal (Ib) to 2,3-dimethyl-3-(p-methylphenyl)-1-butanal (IIIb) was 93:7. Ib could readily be separated from IIIb by distillation.

Pure 4-methyl-4-(p-methylphenyl)-1-pentanal was obtained in a yield of 82% of theory, based on IIb. Bp. 114° C./1 mbar; $n_D^{25}$1.5138

IR (film): 2964, 2925, 2873, 1724, 1516, 1456, 1388, 1366, 818, 588 cm$^{-1}$ $^1$H-NMR (CDCl$_3$): δ=9.58 (s, 1H), 7.4–7.1 (m, 4H), 2.31 (s, 3H), 2.2 (t, 2H), 1.92 (t, 2H), 1.02 (s, 6H) ppm.

MS (m/e): M+ =190 (16%), 152 (2%), 142 (1.5), 133 (100), 115 (4), 105 (21), 93 (6), 77 (4), 65 (3), 51 (1), 41 (9).

Fragrance: interesting aromatic note.

EXAMPLE 3

The procedure described in Example 1 was followed, except that, instead of 710 g of IIb, 889 g of 3-methyl-3-(p-tert-butylphenyl)-1-butene were used for the hydroformylation reaction.

4-Methyl-4-(p-tert-butylphenyl)-1-pentanal of Bp. 135° C./1.0 mbar was obtained in a yield of 81% of theory.

$n_D^{25}$ 1.5080

IR (film): 2963, 2900, 2870, 1725, 1512, 1402, 1363, 1271, 832, 583 cm$^{-1}$ $^1$H-NMR (CDCl$_3$) δ=9.5 (s, 1H), 7.2–7.0 (m, 4H), 2.2 (t, 2H), 1.94 (t, 2H), 1.31 (s, 6H), 3.0 (s, 9H) ppm.

MS (m/e): M+ =232 (9%), 175 (100), 160 (10), 145 (8), 131 (4), 117 (5), 105 (3), 91 (6), 81 (4), 69 (2), 57 (26), 41 (13).

Fragrance: greenish camphorous fragrance with a slightly herbaceous note.

EXAMPLE 4

2,4-dimethyl-4-phenyl-1-pentanal

A stirred mixture of 826 g (3 moles) of 4-methyl-4-phenyl-1-pentanal, 95 g of paraformaldehyde, 500 ml of H$_2$O and 42 g of a previously prepared enamine of 4-methyl-4-phenyl-1-pentanal and piperidine, as a catalyst, was refluxed for 2 hours.

Thereafter, the mixture was cooled, the aqueous phase was separated off, the organic phase was diluted with methanol (1:1), 80 g of a Pd/Al$_2$O$_3$ catalyst were added and hydrogenation was carried out in a 3 l autoclave for 3 hours under an H$_2$ pressure of 25 bar, for 4 hours under an H$_2$ pressure of 35 bar, for 4 hours under an H$_2$ pressure of 45 bar and for 4 hours under an H$_2$ pressure of 55 bar. Thereafter, the autoclave was let down and the mixture worked up by distillation.

The desired 2,4-dimethyl-4-phenyl-1-pentanal was obtained in a yield of 77%, based on 4-methyl-4-phenyl-1-pentanal used.

Bp. 86° C./0.3 mbar, $n_D^{25}$ 1.5070

IR (film): 2965, 2933, 2875, 1724, 1497, 1456, 1477, 1368, 766, 701 cm$^{-1}$.

$^1$H-NMR (CDCl$_3$): δ=0.9 (d, 3H), 1.31 (s, 3H), 1.33 (s, 3H), 1.5–1.6 (m, 1H), 2.1–2.35 (m, 2H), 7.1–7.5 (m, 5H), 9.26 (s, 1H) ppm.

MS (m/e): M+ =190 (4%), 157 (2%), 134 (8), 119 (100), 105 (7), 91 (36), 77 (5), 65 (2), 51 (2), 41 (16).

Fragrance: interesting herbaceous woody note.

We claim:

1. A 4-methyl-4-phenyl-1-pentanal of the formula I

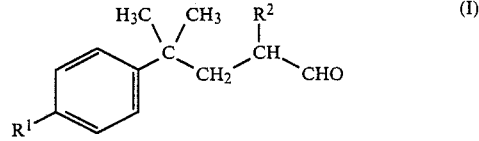

where R$^1$ is hydrogen or C$_1$–C$_4$-alkyl and R$^2$ is hydrogen or methyl, with the proviso that 4-methyl-4-phenyl-1-pentanal is excluded.

2. A process for imparting fragrance properties to, or improving or modifying the fragrance properties of, perfumes and perfumed products, which comprises adding an effective amount of a 4-methyl-4-phenyl-1-pentanal of the formula I to said perfumes and perfumed products.

3. A scent composition containing an effective amount of a 4-methyl-4-phenyl-1-pentanal of the formula I.

4. The scent composition of claim 3, containing from 1–50% by weight of said 4-methyl-4-phenyl-1-pentanal.

5. A process for imparting fragrance properties to, or improving or modifying the fragrance properties of, perfumes and perfumed products, which comprises adding an effective amount of 4-methyl-4-phenyl-1-pentanal to said perfumes and perfumed products.

6. A scent composition containing an effective amount of 4-methyl-4-phenyl-1-pentanal.

7. 2,4-dimethyl-4-phenyl-1-pentanal.

8. 4-methyl-4-(p-methylphenyl)-1-pentanal.

9. 4-methyl-4-(p-tert-butylphenyl)-1-pentanal.

* * * * *